United States Patent [19]
Sisti et al.

[11] Patent Number: 5,973,170
[45] Date of Patent: Oct. 26, 1999

[54] C-7 METAL ALKOXIDES OF BACCATIN III

[75] Inventors: Nicholas J. Sisti, Pepperell, Mass.; Charles S. Swindell, Merion, Pa.

[73] Assignees: NaPro BioTherapuetics, Inc., Boulder, Colo.; Bryn Mawr College, Bryn Mawr, Pa.

[21] Appl. No.: 09/252,739

[22] Filed: Feb. 19, 1999

Related U.S. Application Data

[60] Continuation-in-part of application No. 08/922,684, Sep. 2, 1997, which is a division of application No. 08/719,488, Sep. 25, 1996, Pat. No. 5,750,737.

[51] Int. Cl.⁶ .................................................. C07D 305/14
[52] U.S. Cl. ............................................ 549/510; 549/511
[58] Field of Search ...................................... 549/510, 511

[56] References Cited

U.S. PATENT DOCUMENTS 5,229,526  7/1993  Holton et al. ........................... 549/213
5,684,175  11/1997  Sisti et al. ................................ 560/27

OTHER PUBLICATIONS

"A Chemoselective Approach to Functionalize the C–10 Position of 10–Deacetylbaccatin III Synthesis and Biological Properties of Novel C–10 Taxol Analogues", Kant et al, *Tetrahedron Letters*, vol. 35, No. 31, pp. 5543–5546 (1994).

*Primary Examiner*—Ba K. Trinh
*Attorney, Agent, or Firm*—Timothy J. Martin; Michael R. Henson; Mark H. Weygandt

[57] ABSTRACT

A chemical compound having the formula:

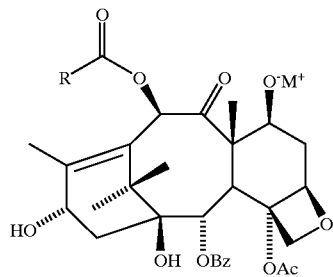

wherein R is an alkyl group and $M^+$ counterion is an alkali metal, and a process of making the same.

17 Claims, No Drawings

C-7 METAL ALKOXIDES OF BACCATIN III

RELATED APPLICATIONS

This is a continuation-in-part of application Ser. No. 08/922,684, filed on Sep. 2, 1997, pending, which is a division of application Ser. No. 08/719,488, filed on Sep. 25, 1996, now U.S. Pat. No. 5,750,737, entitled "Method for Paclitaxel Synthesis".

FIELD OF THE INVENTION

The present invention is directed to intermediates useful in the production of the anti-neoplastic compound paclitaxel. More particularly, it is directed to the C-7 metal alkoxides of baccatin III and analogs thereof, as well as methods of producing the same.

BACKGROUND OF THE INVENTION

Various taxane compounds are known to exhibit anti-tumor activity. As a result of this activity, taxanes have received increasing attention in the scientific and medical community. Primary among these is a compound known as "paclitaxel" which is also referred to in the literature as "taxol". Paclitaxel has been approved for the chemotherapeutic treatment of several different varieties of tumors, and the clinical trials indicate that paclitaxel promises a broad range of potent anti-leukemic and tumor-inhibiting activity. Paclitaxel has the formula:

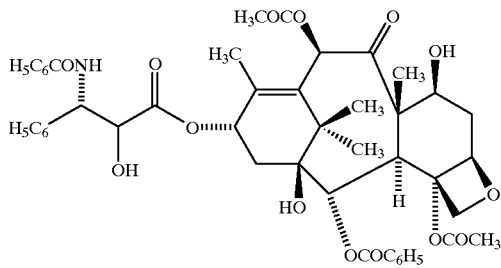

Paclitaxel is a naturally occurring taxane diterpenoid which is found in several species of the yew (genus Taxus, family Taxaceae). Unfortunately, the concentration of this compound is very low. The species of evergreen are also slow growing. Even though the bark of the yew trees typically exhibit the highest concentration of paclitaxel, the production of one kilogram of paclitaxel requires approximately 16,000 pounds of bark. Thus, the long term prospects for the availability of paclitaxel through isolation are discouraging.

While the presence of paclitaxel in the yew tree is in extremely low concentrations, there are a variety of other taxane compounds, such as Baccatin III, cephalommanine, 10-deacetylbaccatin III, etc., which are also able to be extracted from the yew bark. Some of these other taxane compounds are more readily extracted in higher yields. Indeed, a relatively high concentration of 10-deacetylbaccatin III can be extracted from the leaves of the yew as a renewable resource.

In order to successfully synthesize paclitaxel, convenient access to a chiral, non-racemic side chain and an abundant natural source of a usable baccatin III backbone as well as an effective means of joining the two are necessary. However, the esterification of the side chain to the protected baccatin III backbone is difficult because of the sterically hindered C-13 hydroxyl in the baccatin III backbone which is located within the concave region of the hemispherical protected baccatin III skeleton.

One technique for the semi-synthesis of paclitaxel is found in U.S. Pat. No. 5,684,175 to Sisti et al. In that patent, paclitaxel is synthesized by joining C7-TES baccatin III with N-carbamate protected C2' hydroxyl benzyl-type protected (2R,3S)-3-phenylisoserine, where the C2' hydroxyl is protected by a hydrogenable benzyl-type group such as benzyloxymethyl (BOM) or benzyl. Following the esterification of the protected baccatin III and the protected side chain, the compound may be suitably deprotected, acylated, and further deprotected to yield paclitaxel.

While the existing techniques for synthesizing paclitaxel certainly have merit, there is still a need for improved chemical processes which can produce this anti-cancer compound and intermediates useful in the synthesis and semi-synthesis thereof. The present invention is directed to the synthesis of C-7 CBZ protected baccatin III and analogs thereof through a metal alkoxide intermediate. The C-7 CBZ protected baccatin III can then be esterified with a suitably protected side chain, then the resulting compound deprotected to yield paclitaxel or other analogs.

SUMMARY OF THE INVENTION

It is an object of the present invention to provide a new intermediate useful in synthesizing paclitaxel.

It is further an object of the present invention to provide a method of producing a new intermediate compound useful in the production of paclitaxel.

The present invention thus is directed to a new chemical intermediate having the formula

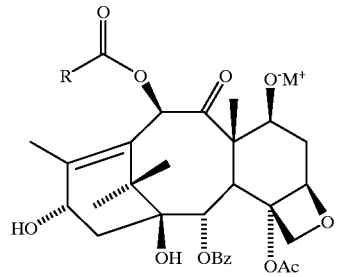

wherein R is an alkyl group and $M^+$ is an alkali metal counterion. The $M^+$ counterion is preferably selected from the group consisting of the lithium counterion, potassium counterion, and sodium counterion. Preferably the alkyl group is a methyl group and $M^+$ is the lithium counterion.

The present invention is further directed to a method of producing a compound having the above formula, wherein R is an alkyl group and the $M^+$ counterion is an alkali metal counterion, from a starting compound which is either baccatin III or 10-deacetylbaccatin III. The method comprises the steps of dissolving the starting compound in a first solvent to form a first solution which is then cooled to a temperature of −20° C. or less. An alkali base is thereafter added to the first solution to form an intermediate compound having a metal alkoxide at the C-7 position. Any of the intermediate compound present in the first solution where the intermediate compound does not already have an acetyl group at the C-10 position is then selectively acylated at the C-10 position.

Preferably, the starting compound is dissolved in tetrahydrofuran (THF), and the first solution is cooled under a nitrogen atmosphere. The alkali base is preferably n-butyl lithium, potassium hydride or sodium hydride. When the starting compound is 10-deacetylbaccatin III, it is preferred that at least two equivalents of the alkali base is added. After the alkali base is added, the first solution is stirred for approximately five minutes. The intermediate compound is selectively acylated by adding an acid chloride, preferably acetyl chloride, or acetic anhydride. A quenching agent, preferably ammonium chloride, may be added to remove excess alkali base and acylating agent. The preferred method is conducted so as to produce a compound wherein R is a methyl group and $M^+$ is $Li^+$.

These and other objects of the present invention will become more readily appreciated and understood from a consideration of the following detailed description of the exemplary embodiments of the present invention, in which:

DETAILED DESCRIPTION OF THE INVENTION

The present disclosure is broadly directed to new chemical compounds, namely, C-7 metal alkoxides of baccatin III and analogs thereof. The invention also concerns a method of producing these chemical compounds. Such compounds are demonstrably useful for the efficient production of paclitaxel and paclitaxel analogs. More specifically, the present invention discloses C-7 metal alkoxides of baccatin III as useful intermediates in the synthesis of C-7 CBZ baccatin III, which is a useful intermediate in the production of paclitaxel. The C-7 CBZ baccatin III may be esterified with an N-CBZ-3-phenylisoserine acid having a hydrogenable benzyl-type hydroxyl protecting group at C-2' to join the side chain at the C-13 hydroxyl of the protected baccatin III backbone. The general processes described herein involve the production of the C-7 CBZ baccatin III backbone through the C-7 metal alkoxide intermediate, the condensation of the C-7 CBZ baccatin III backbone with a suitably protected N-CBZ-3-phenylisoserine acid having the hydrogenable benzyl-type protecting group at C-2', and the subsequent deprotection to yield paclitaxel.

A. Production of C7-CBZ Protected Baccatin III through the C-7 Metal Alkoxide Intermediate According to the present invention, two alternative routes are described for producing C-7 CBZ protected baccatin III. On one hand, baccatin III can be protected at the C-7 site to yield C-7 CBZ baccatin III. On the other hand, 10-deacetylbaccatin III (10-DAB) can be directly converted to C-7 CBZ baccatin III without going through a baccatin III intermediate. Production from baccatin III is advantageous for its yield and simplicity.

The method using 10-deacetylbaccatin III has an advantage since 10-deacetylbaccatin III is much more naturally abundant, and thus less expensive, than baccatin III; however, this alternative method has a reduced yield.

Route I (Using baccatin III)

C-7 CBZ baccatin III has the formula:

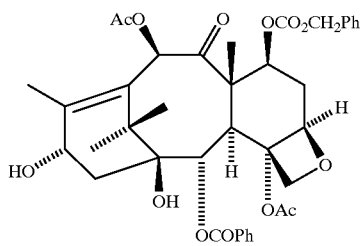

and can be synthesized from baccatin III according to the following reaction:

Reaction I

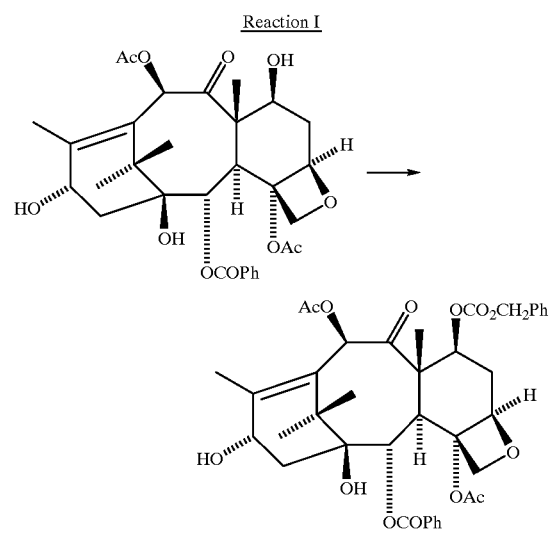

Baccatin III is dissolved in anhydrous THF (tetrahydrofuran) to form a first solution, which is cooled under a nitrogen atmosphere to a reduced temperature of less than −20° C. n-Butyl lithium (1.6 M in hexane) is then added dropwise to the first solution to form a second solution, which is stirred for approximately five minutes at the reduced temperature. This creates the C-7 lithium alkoxide of baccatin III:

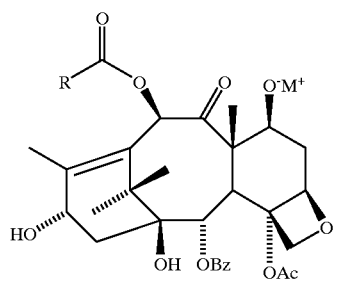

where $M^+=Li^+$, and $R=CH_3$.

Benzyl chloroformate (CBZ-Cl) is added dropwise to the second solution to form a third solution which is then stirred and allowed to warm to 0° C. over approximately one hour. The third solution is quenched with cold saturated ammonium chloride to eliminate any excess n-butyl lithium and CBZ-Cl, and the mixture is concentrated under vacuum to yield a first residue. This first residue is next taken up in ethyl acetate and washed once with water to remove unwanted salts. Next, the residue is washed with brine. The organic layer is then dried and concentrated under vacuum to yield a second residue. The second residue is recrystallized or column chromatographed with ethyl acetate: hexane to give C-7 CBZ baccatin III as a white solid.

The ordinarily skilled artisan would understand that instead of using n-butyl lithium, it is possible to use other alkali bases, especially potassium hydride and sodium hydride to form the corresponding C-7 metal alkoxide of baccatin III:

where $M^+ = Li^+$, $K^+$, $Na^+$, or another alkali metal, and $R=CH_3$.

Route 2

(Using 10-deacetylbaccatin III)

Alternatively, C-7 CBZ baccatin III can be synthesized directly from 10-deacetylbaccatin III as follows:

Reaction II

Here, 10-DAB is dissolved in THF to form a first solution which is cooled to a reduced temperature of less than −20° C. under a nitrogen atmosphere. At least two equivalents of n-butyl lithium (1.6 M in hexane)—or another alkali base, as described above—are then added dropwise to the first solution to form a second solution which is then stirred for approximately five minutes at the reduced temperature. Preferably, acetyl chloride (one equivalent) is added to the second solution to form a third solution which is stirred at the reduced temperature for approximately thirty minutes. Alternatively, acetic anhydride (one equivalent) may possibly be used in place of the acetyl chloride to acylate the 10-DAB.

In either case, benzyl chloroformate (one equivalent) is next added, and this fourth solution is stirred for an additional thirty minutes at the reduced temperature and then warmed to 0° C. over thirty minutes. The fourth solution is then quenched with cold saturated ammonium chloride at the reduced temperature to remove any excess n-butyl lithium, acetyl chloride and CBZ-Cl; this mixture is then warmed to room temperature. The solvent is removed under vacuum to yield an initial residue which is taken up in ethyl acetate and washed with water to remove unwanted salts. The residue is then washed with brine, dried and concentrated under vacuum to yield a final residue. The final residue is chromatographed (silica gel hexanes:ethyl acetate) to yield C-7 CBZ baccatin III. It is important to note that this method represents a direct synthesis of C-7 CBZ baccatin III from 10-DAB, as the intermediate formed in this reaction is a C-7 lithium alkoxide of baccatin III; that is, the intermediate is not baccatin III itself.

While both Routes 1 and 2 specifically are directed to the production of baccatin III, it should be apparent to the ordinarily skilled person that baccatin III analogs can be produced from the Route 2 process simply by substituting the appropriate acid chloride to the second solution in Route 2. This would result in the formation of analogues with different alkyl groups at C-10. The resulting intermediate in the process is:

where $M^+ = Li^+$, $K^+$, $Na^+$, or another alkali metal, and R is $CH_3$ or another alkyl group.

It should now be appreciated that both Route 1 and Route 2 to the production of C-7 CBZ baccatin III can be expressed as a generalized method. This method starts with a step of dissolving a starting compound selected from a group consisting of baccatin III and 10-deacetylbaccatin III in a first solvent to form a first solution. The first solution is then cooled to a temperature of −20° C. or less. Thereafter, an alkali base is added to the first solution thereby to form an intermediate compound having a metal alkoxide at the C-7 position thereof. Next, as would be required for the 10-DAB starting compound, the method includes selectively acylating, at the C-10 position, any of the first intermediate compound present in the first solution where the intermediate compound does not already have an acetyl group at the C-10 position thereby to produce a second solution of C-7 metal alkoxide of baccatin III. Alternatively, the first intermediate compound may be acylated with the appropriate acid chloride to form analogues with various alkyl groups at C-10. Of course, where the starting compound is baccatin III, the C-10 position already has an acetyl group. In any event, the method may include a step of thereafter adding CBZ-Cl to the second solution to form a third solution of C-7 CBZ baccatin III.

B. Production of the 3-Phenylisoserine Side Chain

The production of the C3' N-CBZ C-2' benzyl-type protected (2R,3S)-3-phenylisoserine side chain has been previously disclosed in U.S. Pat. No. 5,684,175 to Sisti et al., which is entitled "C-2+ Hydroxyl-Benzyl Protected, N-Carbamate Protected (2R,3S)-3-Phenylisoserine and Production Process Therefor". This compound has the general formula:

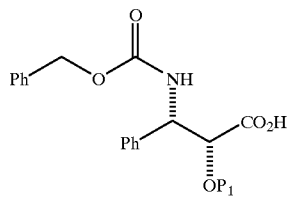

Here, the $P_1$ protecting group on the C-2' hydroxyl is a hydrogenatable protecting group such as benzyloxymethyl (BOM) or benzyl.

C. Esterification of C-7 CBZ Baccatin III and the Side Chain

Esterification of C-7 CBZ baccatin III with the C-3' N-CBZ C-2'-protected (2R,3S)-3-phenylisoserine side chain (where the C-2' hydroxyl is protected by any hydrogenable protecting group) may be accomplished as follows. The preferred hydrogenable benzyl group shown below is BOM (benzyloxymethyl). The useful reaction is diagrammed:

Reaction III

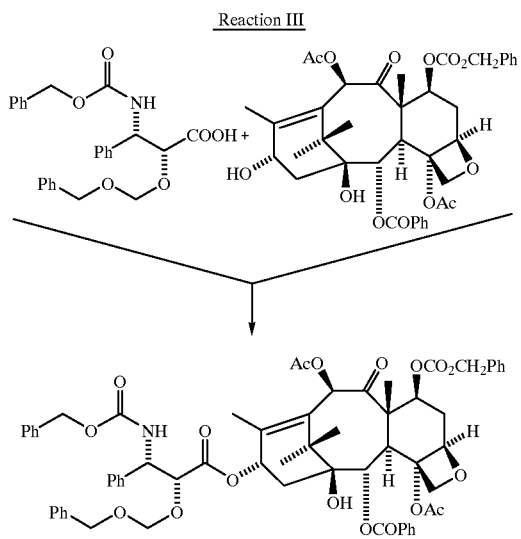

Here the C-7 CBZ baccatin III (one equivalent) and the acid side chain (six equivalents) are dissolved in toluene. To this mixture, 0.5 equivalents of DMAP (dimethylamino pyridine) and preferably six equivalents of dicyclohexylcarbodiimide (DCC) are added, and the resulting mixture heated at 70° C. for thirty minutes to one hour although the range of temperature could be 60° C. to 80° C. It should also be noted, however, that other dialkyl carbodiimides may be substituted for the DCC, with one example being diisopropylcarbodiimide.

Next, the solution is cooled to room temperature and an equal volume of ethyl acetate or diethyl ether is added to the solution. The resulting mixture is then cooled to 0° C. and held at this temperature for twenty-four hours. After this time it is filtered, and the residue is rinsed with either diethyl ether or ethyl acetate. The combined organics are then washed with hydrochloric acid (5%), water, and finally brine. The organic phase is separated, dried and concentrated under vacuum. The resulting residue is then dissolved in ethyl acetate:hexane and eluted over a silica gel plug. The eluent is then concentrated under vacuum to result in the esterified compound:

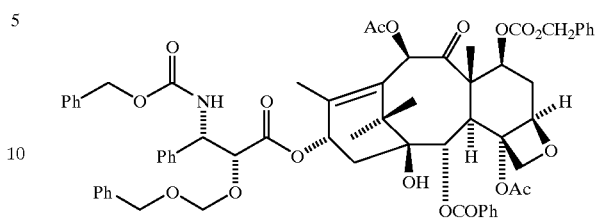

D. Deprotection to Paclitaxel

The esterified compound, above, may now be converted into paclitaxel by removing the nitrogen and C-7 CBZ groups, putting the benzoyl group onto the nitrogen, and finally removing the C-2' benzyl-type protecting group. Removal of the CBZ groups, and subsequent addition of the benzoyl group to the nitrogen are accomplished as follows (BOM is shown as the protecting group at the C-2' hydroxyl site, although benzyl could also be used):

Reaction IV

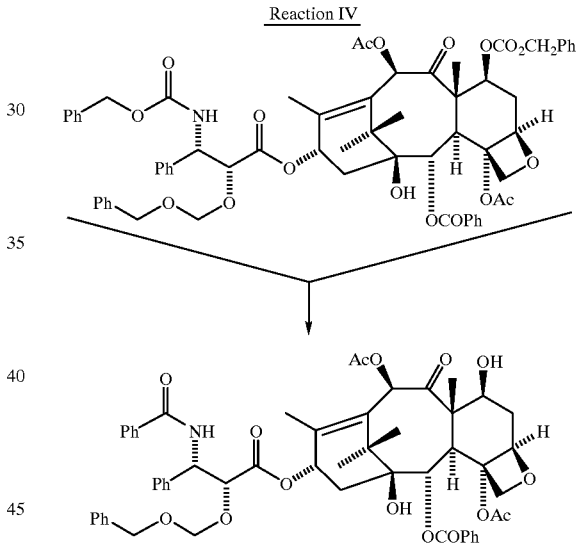

Here, the coupled product is dissolved in isopropanol to which the Pearlman's catalyst is added. The resulting mixture is hydrogenated at 40 psi for twenty-four hours, although alternatively, the mixture can be stirred under one atmosphere of hydrogen for twenty-four hours. Thereafter, the mixture is filtered through diatomaceous earth and reduced under vacuum to residue. Preferably, the residue is taken up in toluene and anhydrous potassium carbonate added. Alternatively, the residue may be taken up in ethyl acetate or toluene and a tertiary amine base, such as triethylamine, is added. In either case, benzoyl chloride is then added dropwise, and the mixture stirred for two hours. The resulting mixture is then washed with water and finally brine. The resulting organic phase is then separated, dried, and concentrated under vacuum to yield C-2' BOM paclitaxel.

Finally, the C-2' BOM is removed according to the following reaction:

Reaction V

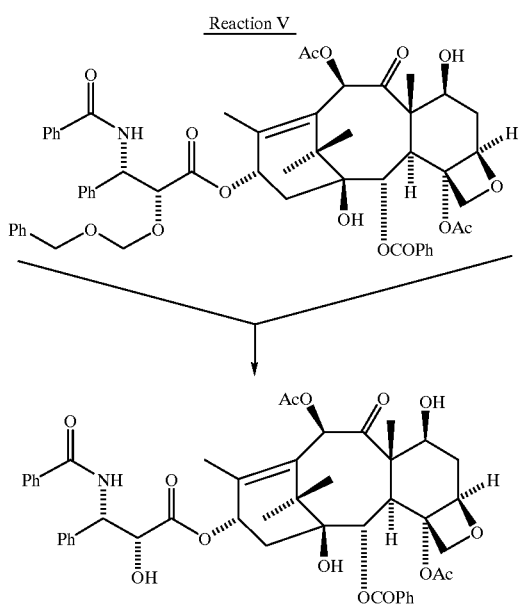

The BOM protected paclitaxel is dissolved in isopropanol to which Pearlman's catalyst is added. This mixture is hydrogenated for twenty-four hours under 40 psi hydrogen to yield paclitaxel.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

We claim:

1. A chemical compound having the formula:

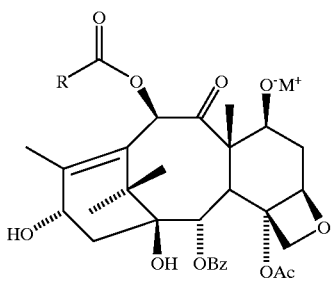

wherein R is an alkyl group and the $M^+$ counterion is an alkali metal counterion.

2. A chemical compound according to claim 1 wherein R is a methyl group.

3. A chemical compound according to claim 1 wherein the $M^+$ counterion is selected from the group consisting of the lithium counterion, potassium counterion and sodium counterion.

4. A chemical compound according to claim 1 wherein the $M^+$ counterion is the lithium counterion.

5. A chemical compound according to claim 1 wherein R is a methyl group and $M^+$ is the lithium counterion.

6. A method of producing a compound having a formula:

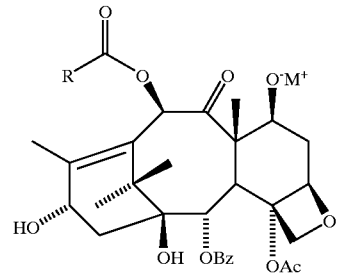

wherein R is an alkyl group and the $M^+$ counterion is an alkali metal counterion, from a starting compound selected from a group consisting of baccatin III and 10-deacetylbaccatin III comprising the steps of:
   (a) dissolving said starting compound in a first solvent to form a first solution;
   (b) cooling the first solution to a temperature of $-20°$ C. or less;
   (c) thereafter adding to the first solution an alkali base to form an intermediate compound having a metal alkoxide at the C-7 position thereof;
   (d) selectively acylating at the C-10 position any of said intermediate compound present in the first solution where the intermediate compound does not already have an acetyl group at the C-10 position.

7. A method of producing a compound according to claim 6 wherein the first solvent is tetrahydrofuran (THF).

8. A method of producing a compound according to claim 6 wherein the step of cooling is conducted under a nitrogen atmosphere.

9. A method of producing a compound according to claim 6 wherein the starting compound is 10-deacetylbaccatin III and at least two equivalents of the alkali base is added to the first solution.

10. A method of producing a compound according to claim 6 wherein the alkali base is selected from the group consisting of n-butyl lithium, potassium hydride and sodium hydride.

11. A method of producing a compound according to claim 6 wherein the first solution is stirred for approximately five minutes after adding the alkali base.

12. A method of producing a compound according to claim 6 wherein the starting compound is 10-deacetylbaccatin III and the step of selectively acylating is accomplished by adding an acid chloride to the first solution.

13. A method of producing a compound according to claim 12 wherein the acid chloride is acetyl chloride.

14. A method of producing a compound according to claim 6 wherein the starting compound is 10-deacetylbaccatin III and the step of selectively acylating is accomplished by adding acetic anhydride to the first solution.

15. A method of producing a compound according to claim 6 including the additional step of quenching the first solution with a quenching agent.

16. A method of producing a compound according to claim 15 wherein the quenching agent is ammonium chloride.

17. A method of producing a compound according to claim 6 wherein R is a methyl group and $M^+$ is $Li^+$.

* * * * *